(12) United States Patent
Tomita et al.

(10) Patent No.: US 7,594,175 B2
(45) Date of Patent: Sep. 22, 2009

(54) PROCESSING INSTRUMENT AND PROCESSING INSTRUMENT SYSTEM

(75) Inventors: Koji Tomita, Hitachinaka (JP); Takashi Noguchi, Machida (JP); Kazuhiko Okuzawa, Hitachinaka (JP); Akira Maekawa, Hitachinaka (JP)

(73) Assignee: Hitach High-Technologies Corporation, Tokyo (JP)

( * ) Notice: Subject to any disclaimer, the term of this patent is extended or adjusted under 35 U.S.C. 154(b) by 462 days.

(21) Appl. No.: 11/348,420

(22) Filed: Feb. 6, 2006

(65) Prior Publication Data

US 2006/0221096 A1    Oct. 5, 2006

(30) Foreign Application Priority Data

Mar. 30, 2005    (JP)    ............................. 2005-098904

(51) Int. Cl.
*G06F 15/00* (2006.01)
*G06F 13/00* (2006.01)
(52) U.S. Cl. ....................................... 715/700; 382/305
(58) Field of Classification Search ................. 715/700, 715/763, 764–765, 853–854; 382/312, 305, 382/302
See application file for complete search history.

(56) References Cited

U.S. PATENT DOCUMENTS

| 7,115,424 B2* | 10/2006 | Nakao ........................... 438/5 |
| 7,280,711 B2* | 10/2007 | Yoshida et al. .............. 382/305 |
| 2004/0190034 A1* | 9/2004 | Ozawa et al. .............. 358/1.13 |

\* cited by examiner

*Primary Examiner*—Kevin Nguyen
(74) *Attorney, Agent, or Firm*—Dickstein Shapiro LLP

(57) ABSTRACT

A processing instrument with configurable processing conditions makes it possible to simplify operations, prevent operation errors, and reuse, without modification, installed software having a track record in operation. An operation terminal includes a research work processing section with software having a track recording in operation that provides a function which receives processing conditions from an input section, a function which executes processing according to processing conditions, and a function which displays results of the processing. A fixed processing condition database stores fixed processing conditions set to a predetermined values. A routine work processing section includes a function for receiving variable processing conditions that are a part of the processing conditions from the input section, a function for creating the processing conditions necessary for the operation terminal by combining the variable and fixed processing conditions, and a function for displaying the result of the processing from the research processing section.

9 Claims, 11 Drawing Sheets

FIG. 4 A
FIG. 4 B
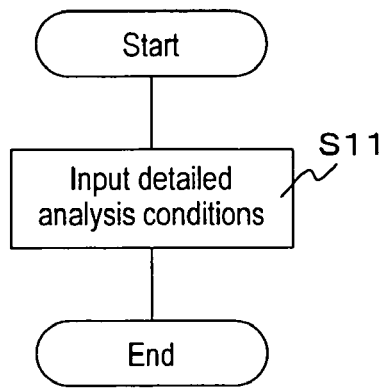
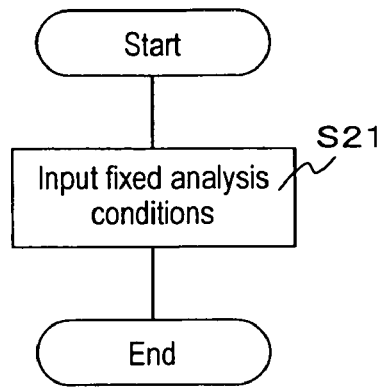
FIG. 4 C
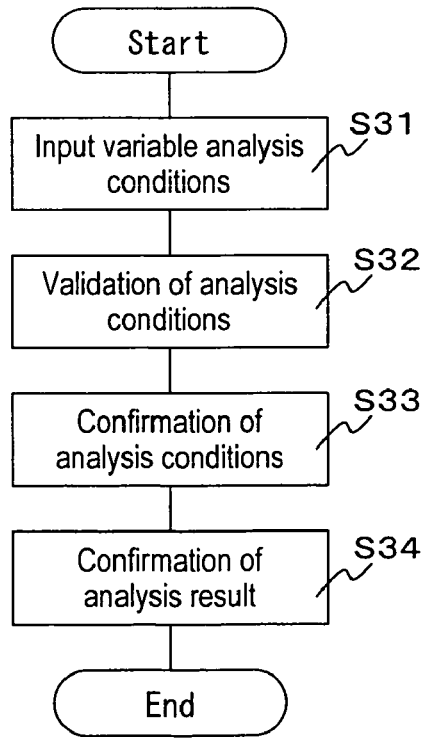

FIG. 8

| 802 | 801 | 803 |
|---|---|---|
| 0x01 | GUI control script storage area for receiving number of usages | |
| 0x02 | GUI control script storage area for receiving liquid amounts | |
| 0x03 | GUI control script storage area for purge | |
| 0x04 | GUI control script storage area for receiving lamp energy value | |
| 0x05 | GUI control script storage area for RG execution | |
| ⋮ | ⋮ | |
| 0x10 | GUI control script storage area for sample addition | |
| 0x11 | GUI control script storage region for sample deletion | |
| 0x12 | GUI control script storage area for method update | |
| 0x13 | GUI control script storage area for continuous analysis execution | |
| 0x14 | GUI control script storage area for receiving continuous analysis status | |
| 0x15 | GUI control script storage area for re-analysis execution | |
| ⋮ | ⋮ | |

PROCESSING INSTRUMENT AND PROCESSING INSTRUMENT SYSTEM

CLAIM OF PRIORITY

The present application claims priority from Japanese application JP 2005-98904 filed on Mar. 30, 2005, the content of which is hereby incorporated by reference into this application.

FIELD OF THE INVENTION

The present invention relates to a processing instrument which receives processing conditions and executes a processing, specifically, to a processing instrument and a processing instrument system for specific services which are able to make detailed processing conditions be set to execute various kinds of processing and achieve simplification of operations and prevention of operation errors. In processing instruments are included semiconductor equipment manufacturing instruments, clinical instruments, and amino acid analytical instruments, etc. Operation errors in the present invention include an error in the processing conditions and an error in the timing indicating a processing.

BACKGROUND OF THE INVENTION

Recently, in the fields of processing instruments such as semiconductor equipment manufacturing instruments, clinical instruments, and analytical instruments, etc., the performance and functions such as making things finer, having multiple items, high sensitivity, and high speed have been advanced on the one hand, but there has been an increase in the variety of operation modes, on the other hand. According to these trends, setting the processing conditions in detail is required for a processing instrument to make full use of the performance and the functions, and a GUI (Graphical User Interface) which provides a high level graphics function is incorporated in the processing instrument. If such a processing instrument in which a GUI is incorporated is used, a highly skilled operator could execute various kinds of processing, if necessary, because the processing conditions can be set in detail by using an in-depth knowledge concerning the processing instrument including the processing object, hardware, and software. On the other hand, it has been very difficult for operators who have not been well skilled to handle these GUI, so that there have been many examples where they could not use a processing instrument in which such a high performance GUI is incorporated. Moreover, for instance, it has been necessary to improve their skill by letting them spend a long time and acquire the knowledge with the company shouldering a heavy burden of educational expenses. In order to make possible a simplification of the operations and the prevention of operation errors, there is a choice of modifying the software program (hereinafter, called software) which has been accumulating actual results. However, from the viewpoint of ensuring reliability, it has been inconvenient in real situations.

Conventionally, in an on-line type business processing system, the operation of the on-line type business processing system has been made simpler without modifying the business-application software program according to, for instance, a technology described in JP-A, No.55339/1998 (terminal wrapping). Or, the introduction of new software has been achieved by using the technology (API (Application Program Interface) wrapping) which calls an interface command such as an RPC (Remote Procedure Call).

SUMMARY OF THE INVENTION

Although JP-A, No.55339/1998 is predicated on effecting image-display in another calculator by using character string-based user interface control, in general, a processing instrument has no function to perform the character string-based user interface control. Therefore, it is difficult to apply a technology described in JP-A, No.55339/1998 to a processing instrument. Moreover, JP-A, No.55339/1998 is a technology which aims at an improvement in the operation by making the appearance of a GUI better and easier to use, and it does not disclose a technology for a processing instrument which makes possible the simplification of operations and the prevention of operation errors.

Furthermore, in a processing instrument consisting of an operation terminal and an instrument body, software is newly installed and this software accesses the instrument body by using an RPC, resulting in being able to install software in which a GUI function is newly provided. However, an additional function is necessary to support the RPC on the instrument body side, and there has been a problem with respect to efficient reuse in addition to maintaining the quality of the existing software.

The present invention is carried out in order to solve the above-mentioned problems of the prior art, and it is the objective to reuse software having a long track record in operation which is installed in the processing instrument without modification, and to make possible the simplification of operations and the prevention of operation errors.

In order to achieve the aforementioned objective, a processing instrument of the present invention comprises an input section, a display section, a first processing section having a function which receives detailed processing conditions from the input section, a function which executes the processing according to the detailed processing conditions, and a function which displays the result of the processing in the display section, a fixed processing condition data base in which fixed processing conditions set to predetermined values are stored, a second processing section having a function which receives variable processing conditions which are a part of the detailed processing conditions from the input section, a function which creates detailed processing conditions necessary for the first processing section by combining the variable processing conditions and the fixed processing conditions received from the fixed processing condition data base, a function which sends the created detailed processing conditions to the first processing section, and a function which receives a display content of the result of the processing from the first processing section and displays it in the display section.

The second processing section sends the created detailed processing conditions to the first processing section by using a user interface message and receives the display content of the result of the processing from the first processing section.

According to the present invention, if fixed processing conditions are set in advance to be predetermined values, the processing instrument can accomplish a processing based on the fixed processing conditions and the variable processing conditions by using the first processing section which is realized by a user interface software having a track record in operation only by receiving the variable processing conditions from a user via the second processing section. Moreover, since the progress of the processing and the result of the processing, which were accomplished by using the first processing section based on the fixed processing conditions and the variable processing conditions, can be presented to the user via the second processing section, one can achieve the reuse of software having a long track record in operation which is installed in the processing instrument without modification and to make possible the simplification of operations and the prevention of operation errors.

BRIEF DESCRIPTION OF THE DRAWINGS

FIG. 4A is a basic operation flow chart in routine work.
FIG. 4B is a basic operation flow chart in routine work.
FIG. 4C is a basic operation flow chart in routine work.

FIG. 8 is a drawing illustrating a GUI control script storage table stored in a GUI control script data base.

DETAILED DESCRIPTION OF THE PREFERRED EMBODIMENT

Figure 1:
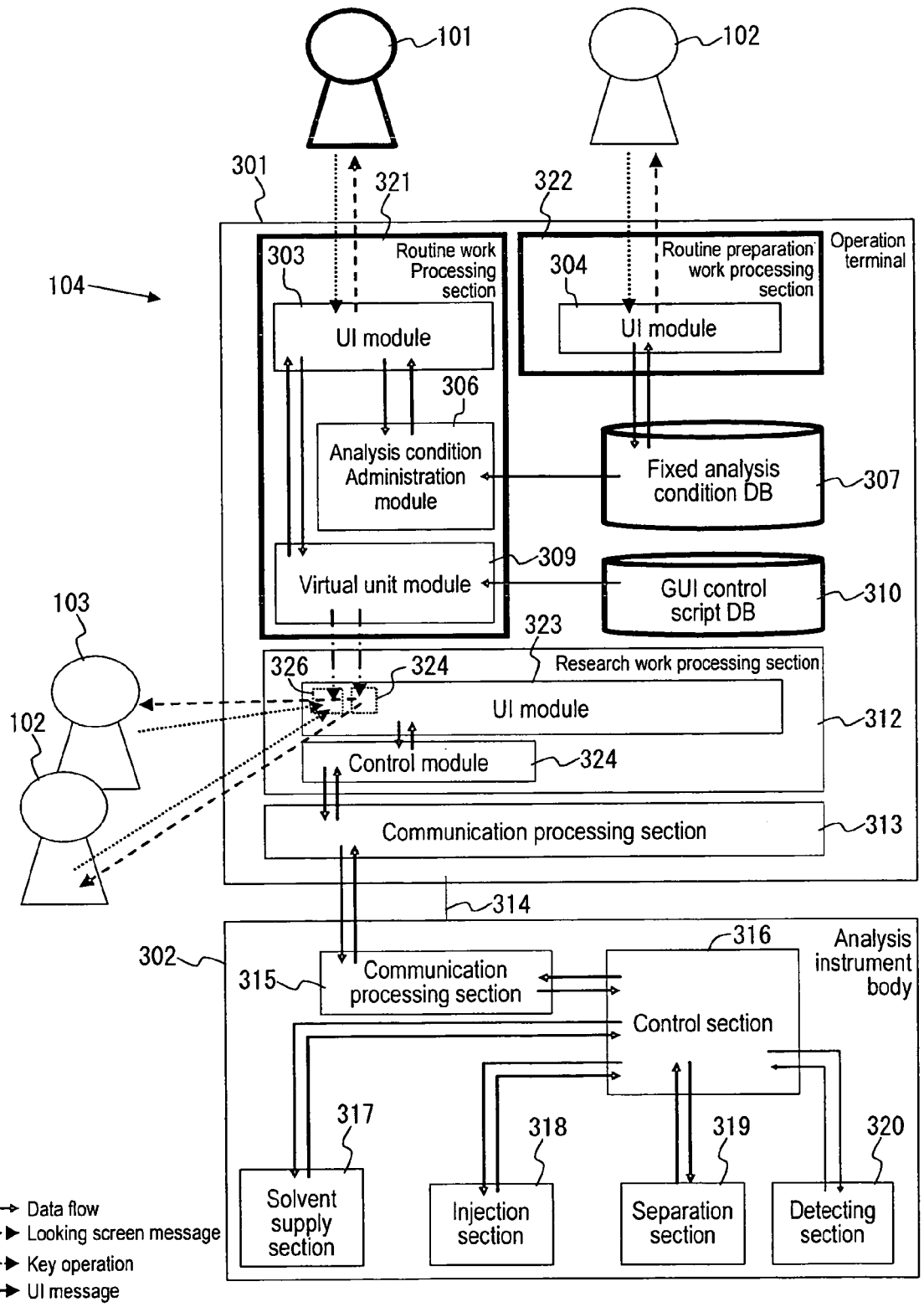
FIG. 1 is a system block diagram of an amino acid analysis instrument.

Hereinafter, the embodiments of the present invention will be described with reference to the accompanying drawings. In this embodiment, an example will be described in which the present invention is applied to an amino acid analytical instrument. The amino acid analytical instrument in this embodiment means an instrument in which amino acids can be analyzed quantitatively and qualitatively. The present invention also can be applied to a processing instrument in addition to an amino acid analytical instrument, and it is a processing instrument equipped with a GUI to receive analytical conditions via a mouse and a keyboard and display the progress of the analysis and the result of the analysis in a display. And, specifically, the present invention can be applied to any processing instrument which can achieve the same effects as a keyboard operation by using a user interface message and can read the data shown in the display whatever the field, the function, the performance, and the configuration. In this embodiment, these conditions are assumed to be satisfied by adopting Windows as the operating system and using SendMessage API as a means of achieving the user interface message.

In a conventional amino acid analytical instrument, detailed analytical conditions can be set, and according to these, if there is a researcher having a high degree of skill, analytical results which are necessary for the accomplishment of the research work could be obtained. For instance, in each sample, a researcher could specify the sample information which indicates the injection volume and the dilution factor, etc., the gradient table information which indicates the ratio of the solvent which is flowing by using a pump, the time change, and the solvent temperature, etc., the waveform processing table information which indicates the waveform processing technique and the time zone to which the processing is applied, etc., and the composition table information which indicates the way to make the working curve, the retention time, and the concentration of the sample, etc. However, while a researcher can specify the analytical conditions in detail, selection of the menu, inputting of the values, and pressing the execution button have to be carried out using these complicated screens even in the case when a routine analyst who does not have a high level of skill has to perform the routine work using processing conditions used in general, because a lot of menus, input items, and buttons are crammed together and displayed on the screen of the amino acid analysis instrument, so that it has been difficult to make possible the simplification of operation and the prevention of operation errors. In this embodiment, an amino acid analysis instrument will be described, in which the aforementioned problems present in a conventional amino acid analysis instrument are solved by reusing the software efficiently without modifying the software installed in the conventional amino acid analysis instrument.

FIG. 1 is a system block diagram illustrating an amino acid analysis instrument 104 to which the present invention is applied. The amino acid analysis instrument 104 consists of an operation terminal 301 and an analysis instrument body 302 connected to each other by using a communication cable 314. The operation terminal 301 comprises a research work processing section 312, a routine work processing section 321, a routine preparation work processing section 322, a fixed analytical condition data base 307, and a GUI control script data base 310. The research work processing section 312 comprises a UI (User Interface) module 323, a processing module 324, and a communications module 313. Moreover, the routine work processing section 321 comprises a UI module 303, an analytical condition administration module 306, and a virtual unit module 309. The routine preparation work processing section 322 comprises a UI module 304. The analysis instrument body 302 comprises a communications processing section 315 which enables communication with the operation terminal 301, a solvent supply section 317, an injection section 318, a separation section 309, a detecting section 320, and a control section 316 which enables control of the lower level instruments. The functions of the research work processing section 312, the routine work processing section 321, the routine preparation work processing section 322 of the aforementioned operation terminal 301 are achieved by the software. As shown in the system block diagram, the amino acid analysis instrument 104 of the present invention consists of a processing section which is achieved by the software having a track record in operation shown as the fine line and a processing section which is achieved by the software newly installed in the present invention shown as the thick line. Hereinafter, an overview with regard to the cooperation between the processing sections will be described.

First of all, an overview with regard to the cooperation between the processing sections will be described which can be achieved by the software having a track record in operation. The UI module 323 consisting of the research work processing section 312 comprises an input column 326 which receives the key operations and an output column 327 which outputs data based on the key operations. The UI module 323 receives the detailed analytical conditions via the input column 326, stores it, creates an upper level command group (hereinafter, written as an upper level command group) to control the analysis instrument body 302 based on the detailed analytical conditions, controls the analysis instrument body 302 to accomplish the analysis of the sample by delivering the upper level command group to the analysis instrument body 302 via the communication processing section 313, receives the progress of the analysis (hereinafter, written as analysis progress) and the result of the analysis (hereinafter, written as analysis result) from the analysis instrument body 302, and displays the stored detailed analytical conditions, the analysis progress, and the analysis result based on the detailed analytical conditions in the output column 327. Concretely, the analysis instrument body 302 receives the aforementioned upper level command group via the communication processing section 315 and analysis of the sample is accomplished by controlling each hard configuration element such as the solvent supply section 317, the injection section 318, the separation section 319, and the detecting section 320 in the control section 316. The analysis progress and the analysis result obtained in the process of the analysis are sent to the operation terminal 301 via the communication processing section 315. The processing module 324 receives the analysis progress and the analysis result via the communication processing section 313 and transfers them to the UI module 323. The UI module 323 receives the analysis progress and the analysis result and displays them to the output column 327.

Next, an overview will be described with regard to the cooperation between the processing section which can be achieved by the software newly installed in this embodiment and the processing section which can be achieved by the software having a track record in operation. When the routine work processing section 321 is activated, the routine work processing section 321 activates the research work processing section 312. At this time, since the UI module 323 displays a screen in full-size on the entire screen, the UI of the research work processing section 312 is covered, so that only the UI of the routine work processing section 321 is displayed on the surface. A routine analyst 101 operates only on this routine work processing section 321.

The virtual unit module 309 consisting of the routine work processing section 321 has a function which achieves the same effects of the aforementioned key operations by sending a predetermined user interface message corresponding to the key operations to the UI module 323, and, moreover, it has a function which receives the display contents from the UI module 323 by sending a predetermined user interface message. The user interface message means a message in which a physical operation such as mouse clicking is converted and recognized in the configuration element program of each user interface. When the operating system is Windows, it can be used by Windows functions such as SendMessage ( ) and PostMessage ( ).

The virtual instrument module 309 inputs the detailed processing conditions to the input column 326 of the UI module 323 by using this function, and, moreover, it becomes possible to receive the analysis progress and the analysis result from the output column 327 of the UI module 323 based on the detailed processing conditions. Therefore, it becomes possible to cooperate the processing section which can be achieved by the software newly installed in this embodiment and the processing section which can be achieved by the software having a track record in operation without modifying the software having a track record in operation.

Figure 2:
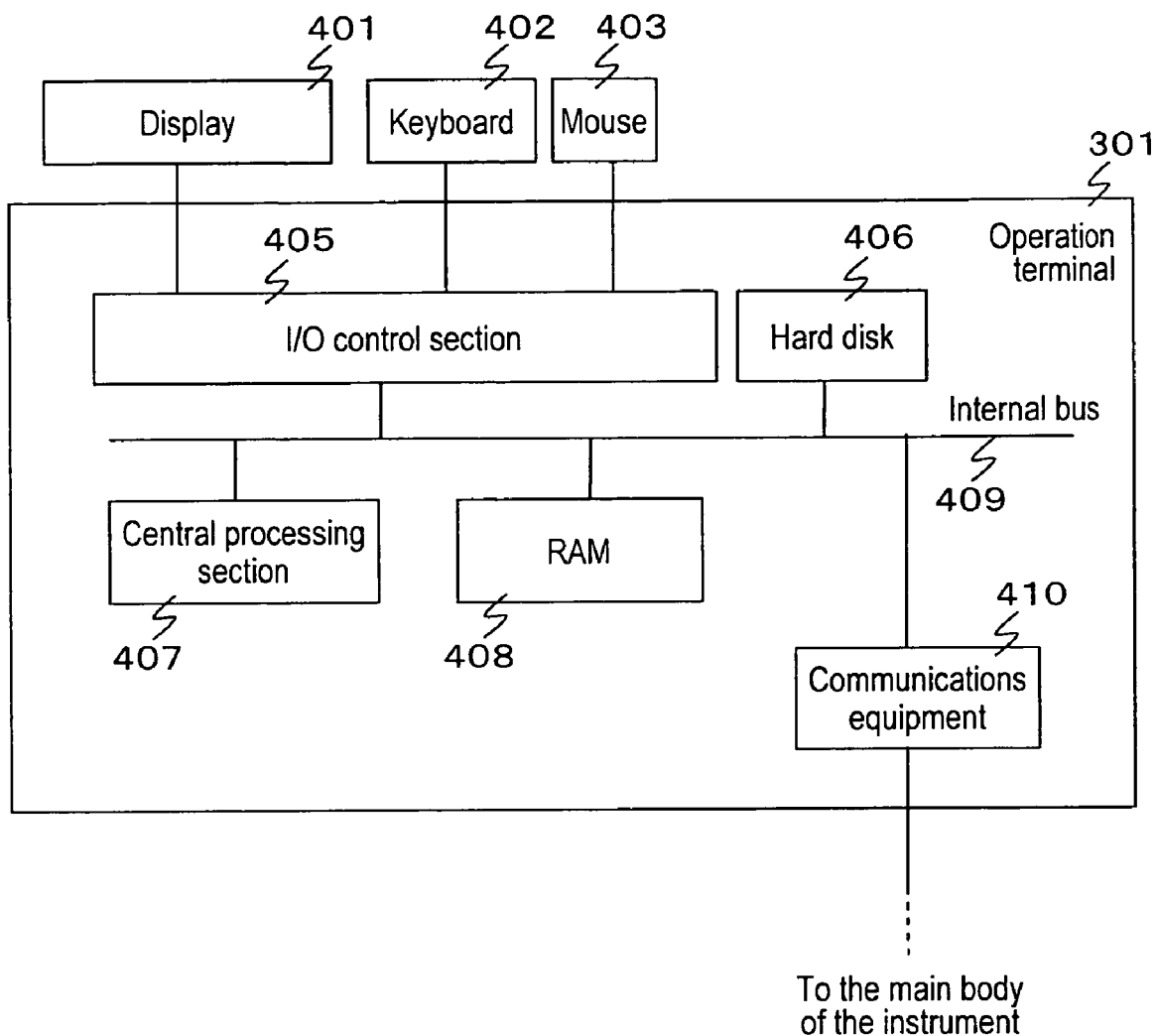
FIG. 2 is a drawing illustrating an example of a hardware configuration of an operation terminal.

FIG. 2 is a drawing illustrating an example of a hardware configuration of the operation terminal 301. The operation terminal 301 of this embodiment comprises a display 401, a keyboard 402, a mouse 403, an I/O control section 405, a hard disk 406, a central processing section 407, RAM (Random Access Memory) 408, an internal bus 409, and communication equipment 410. Software to achieve the routine work processing section 321, software to achieve the routine preparation work processing section 322, software to achieve the research work processing section 312, software to achieve the communication processing section 313, a database of the fixed analytical conditions 307, and a GUI control script data base 310 are stored in the hard disk 406. Moreover, an operating system and control driver software to control the display 401 and the keyboard 402, etc. are stored in the hard disk 406.

Figure 3:
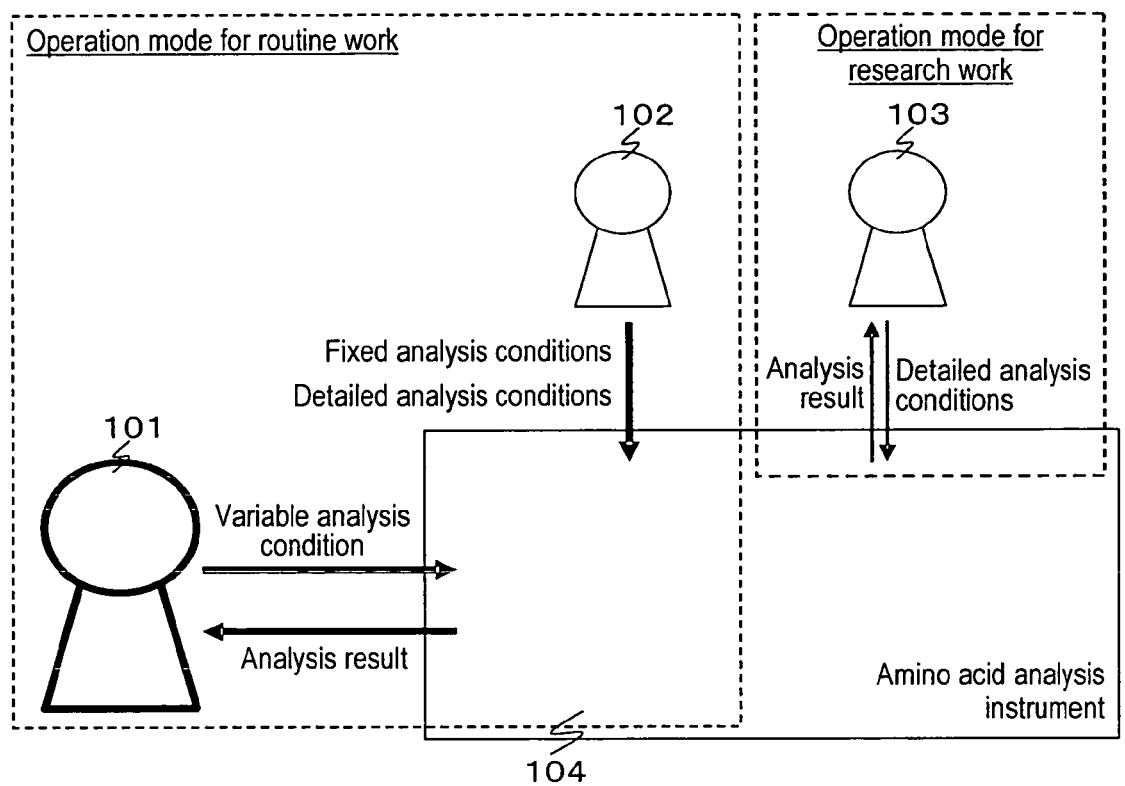
FIG. 3 is a drawing of a utilization image of an amino acid analysis instrument.

FIG. 3 is a utilization image drawing of an amino acid analysis instrument 104 to which the present invention is applied. In order to deal with the two kinds of work, research work and routine work, the amino acid analysis instrument 104 provides two operation modes which are an operation mode for research work and an operation mode for routine work. In the operation mode for research work, a researcher 103 can receive the analysis results which can be used for the research work by specifying the detailed analytical conditions (hereinafter, called detailed analytical conditions) such as a gradient table, a composition table, a waveform processing table, etc. by using the research work software developed for research work (research work processing section). On the other hand, in the operation mode for the routine work, a routine analyst 101 can let the amino acid analysis instrument 104 execute the analysis processing and obtain the analysis results to use the routine work only by specifying minimum analytical conditions (hereinafter, called variable analytical conditions) necessary to be set in the routine work by using routine work software developed for routine work (routine work processing section) and confirming the analysis time and the finish time, etc. calculated by the amino acid analysis instrument 104 based on the aforementioned variable analytical conditions. The variable analytical conditions in this embodiment include the file name of the method file in which the analytical conditions are already set (hereinafter, called method file name). However, setting the analytical conditions such as the default number of the samples which are values fixed in the routine work and the default method file name (hereinafter, called fixed analytical conditions) and the aforementioned detailed analytical conditions should have already been completed before specifying the variable analytical conditions. In this embodiment, it is assumed that the administrator 102 sets the fixed analytical conditions and the detailed analytical conditions by using the routine preparation work software developed for routine preparation work and the research work software. The administrator and the researcher may be the same persons.

FIGS. 4A to 4C are drawings illustrating a basic operation flow for routine work. This operation flow consists of an operation flow 1 by an administrator shown in FIG. 4A, an operation flow 2 by an administrator shown in FIG. 4B, and an operation flow by a routine analyst shown in FIG. 4C. First of all, the operation flow 1 by the administrator shown in FIG. 4A and the operation flow 2 by the administrator shown in FIG. 4B are executed by the administrator. Next, the routine analyst executes the operation flow by the routine analyst shown in FIG. 4C, repeating it an arbitrary number of times. Moreover, after repeating the operation flow by the routine analyst shown in FIG. 4C, the administrator may execute at the appropriate time the operation flow 1 by the administrator shown in FIG. 4A and the operation flow 2 by the administrator shown in FIG. 4B.

In the operation flow 1 by the administrator, the administrator activates the research work processing section and inputs the detailed analytical conditions (S11). The detailed analytical conditions are stored by the research work processing section in the data base that the research work operating section manages. The administrator stops the research work operating section after inputting the detailed processing conditions. In the operation flow 2 by the administrator, the administrator activates the routine preparation work processing section and inputs the fixed analytical conditions (S21). The fixed analytical contusions are stored in the fixed analytical condition database by the routine preparation work processing section. The administrator stops the routine preparation work processing section after inputting the fixed analytical conditions.

In the operation flow by the routine analyst, at first, the routine analyst inputs the variable analytical conditions by using the routine work processing section (S31). Next, the routine analyst refers to the analytical conditions displayed in the operation terminal 301, controls the condition table if necessary, and validates the analytical conditions (S32). The sample name and the quantity of the sample, etc. are updated in the control of the condition table. Next, the routine analyst confirms the analysis progress displayed in the operation terminal 301 (S33). When the analysis is completed, the analysis result is confirmed (S33). The routine analyst can obtain the analysis result only by accomplishing step 31, step 32, and step 33. Therefore, in the process instrument in which the detailed processing conditions can be set one achieves simplification of operations and the prevention of operation errors.

Figure 5:
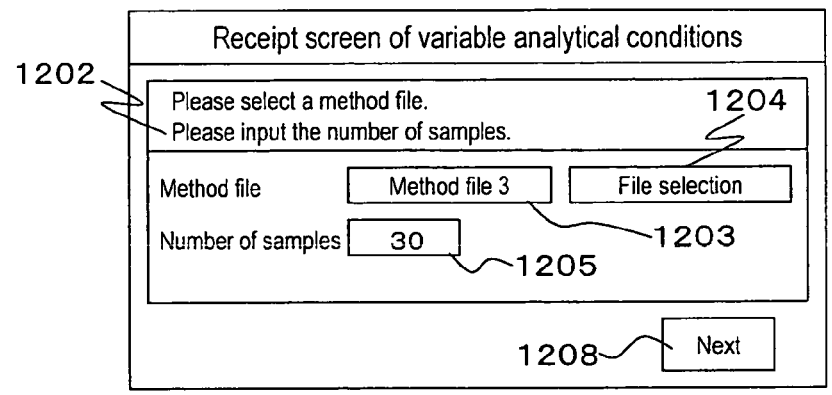
FIG. 5A is a diagram illustrating the screen change provided to a routine analyst in routine work.
FIG. 5B is a diagram illustrating the screen change provided to a routine analyst in routine work.
FIG. 5C is a diagram illustrating the screen change provided to a routine analyst in routine work.
FIG. 5D is a diagram illustrating the screen change provided to a routine analyst in routine work.
Figure 5:
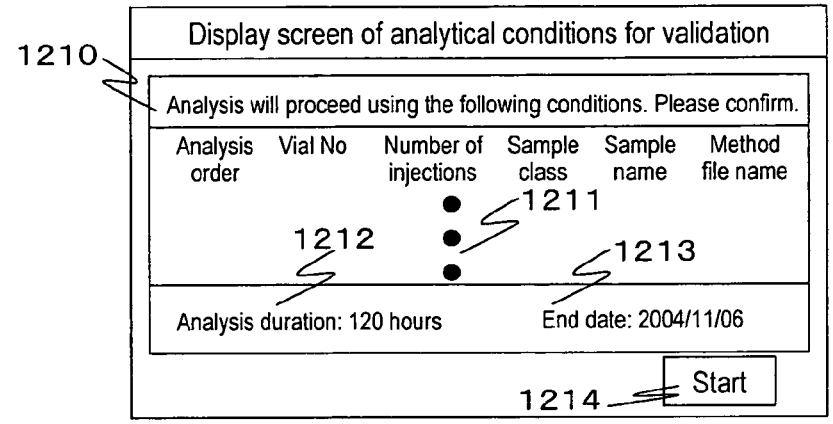
Figure 5:
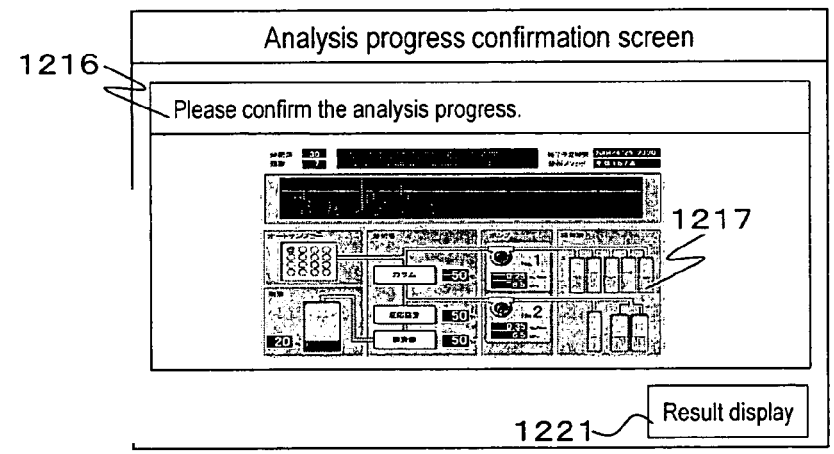
Figure 5:
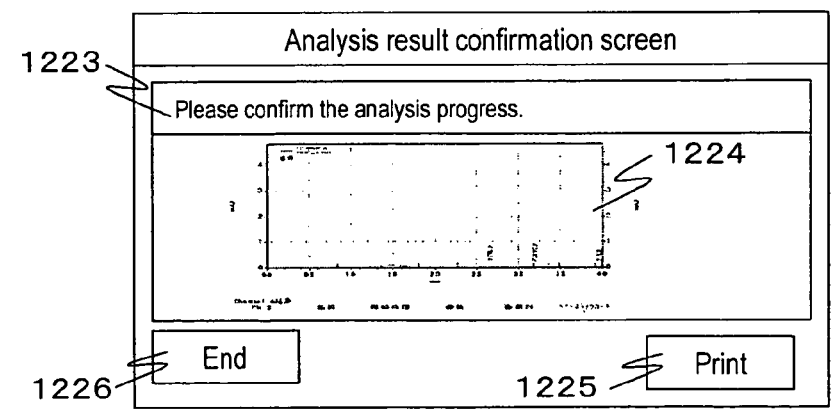

FIGS. 5A to 5D are drawings illustrating the screen transitions provided to the routine analyst in the routine work. FIG. 5A is a receipt screen of the variable analytical conditions provided in step 31, FIG. 5B a display screen of the analytical conditions for validation provided in step 32, FIG. 5C a the analysis progress confirmation screen provided in step 33, and FIG. 5D a analysis result confirmation screen provided in step 34.

The receipt screen of the variable analytical conditions shown in FIG. 5A consists of an operation explanation column 1202 which prompts the selection of a method file and the inputting of a number of samples, a method file output column 1203 for displaying the selected method file, a method file select button 1204 for selecting a method file, a number of samples input column 1205 for inputting the number of samples, and a quasi-confirm button 1208 for tentative definition the analysis conditions. When the quasi-validation button is pressed, the screen is changed from the receipt screen of the variable analytical conditions to the screen of the analytical conditions for validation shown in FIG. 5B.

The display screen of the analytical conditions for validation shown in FIG. 5B consists of an output column for validation 1210 which displays a message to prompt the validation of the analytical conditions, an analytical condition output column for validation 1211 which displays the analytical conditions used for definition, an analysis time output column 1212 which shows the time required to terminate the analysis, a scheduled time output column for analysis termination 1213 which displays the scheduled time of analysis termination, and an analytical condition validation button 1214 for validating the analytical conditions. When the validation button 1214 is pressed, the screen is changed from the display screen of analytical conditions for validation to the analysis status confirmation screen 1215 shown in FIG. 5C. The data output column for validation 1211 has a function to update the analytical conditions. Selected items of the analytical conditions can be edited by selecting the points displaying the analytical conditions that a routine analyst has to update.

The analysis progress confirmation screen shown in FIG. 5C consists of an output column for analysis progress confirmation 1216 which prompts the confirmation of the analysis progress, an analysis progress output column 1217 which displays the analysis progress, and an analysis result display button 1221 which displays the analysis result. A routine analyst presses the analysis result display button 1221 after confirming termination of the analysis in the analysis progress confirmation screen, the screen changes to the analysis result confirmation screen shown in FIG. 5D.

The analysis result confirmation screen shown in FIG. 5D consists of an output column for analysis result confirmation 1223 which displays a message to prompt the confirmation of the analysis result, an analysis result output column 1224 which displays the analysis result, an analysis result print button 1225 which prints out the analysis result, and an end button 1226 which terminates the analysis and returns to the initial screen.

Figure 6:
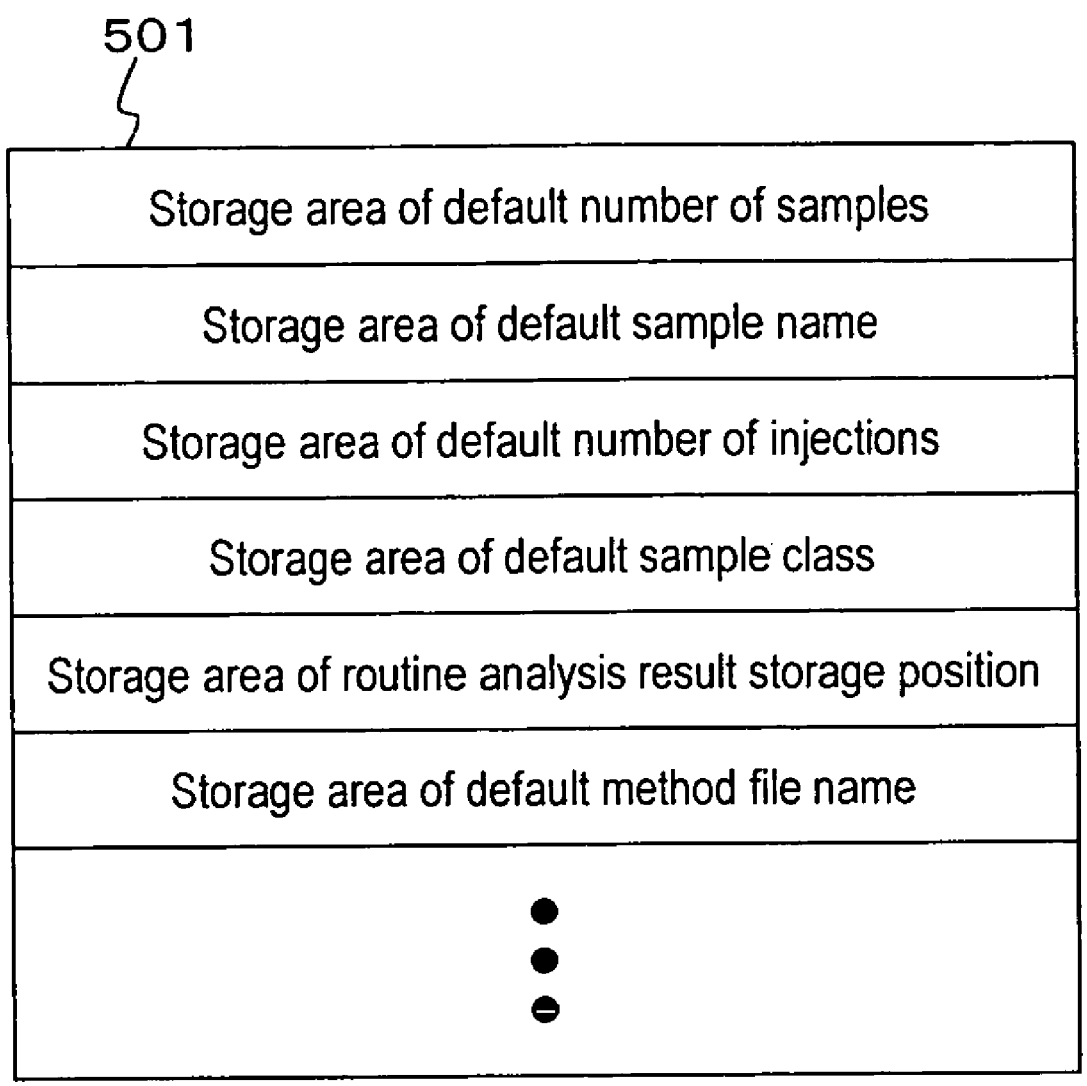
FIG. 6 is a diagram illustrating a fixed analytical condition storage table stored in a fixed analytical condition database.

FIG. 6 shows a fixed analysis condition storage table 501 which is stored in the fixed analysis condition database 307. The fixed analysis condition storage table 501 consists of a storage area of default number of samples for storing the default number of samples, a storage area of default sample name storage area for storing the default sample name, a storage area of default injection amount for storing the default number of injections, a storage area of default sample class for storing the default sample class, a storage area of routine analysis result storage position, and storage area of a default method file name, etc. These contents are stored by the administrator executing the operation flow 2 by the administrator shown in FIG. 4B via the routine preparation work processing section 322 shown in FIG. 1.

Figure 7:
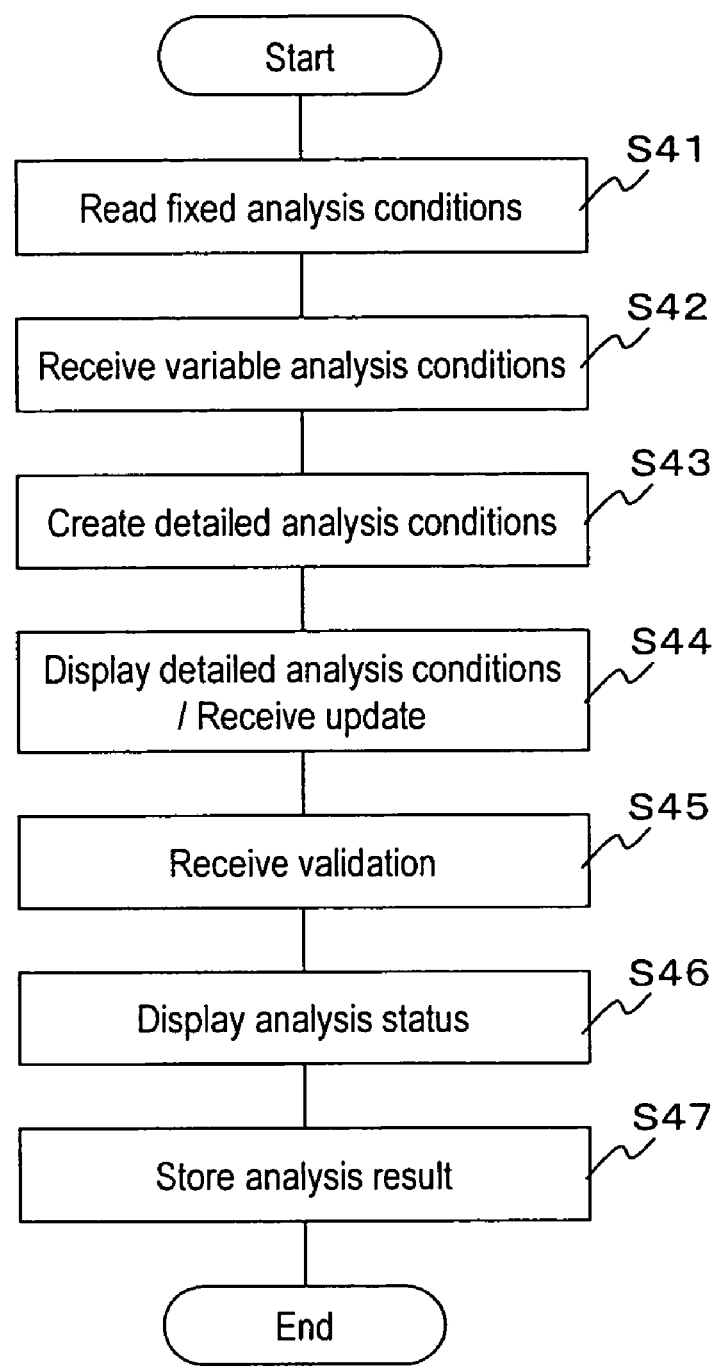
FIG. 7 is a processing flow when an amino acid analysis instrument performs routine analysis processing.

FIG. 7 is a drawing illustrating a process flow in the case when an amino acid analysis instrument 104 executes a routine analysis processing.

First of all, the UI module 303 reads the fixed analytical conditions from the fixed analytical condition table 501 stored in the fixed analytical condition data base 307 by using the analytical condition administration module 306 (S41). Next, the UI module 303 displays the variable analytical condition receipt screen based on the fixed analytical conditions and receives the variable analytical conditions (S42). Next, the UI module 303 creates the detailed analytical conditions which are capable of being received by the research work processing section (software for research work) 312 by using the analytical condition administration module 306 based on the fixed analytical conditions and the variable analytical conditions (S43). Then, the UI module 303 displays the display screen of analytical conditions for validation based on the detailed analytical conditions and receives the update of the detailed analytical conditions (S44). In this embodiment, the update of the detailed analytical conditions is received by displaying a part of the sequence table, which is easily understood by a routine analyst, in the display screen of analytical condition for validation. However, the present invention can be applied even if it is an embodiment which displays other detailed analytical conditions. Next, the UI module 303 receives the validation of the analytical conditions (S45). At this time, in step 45, if an update of the detailed analytical conditions is received, the UI module 303 creates the detailed analytical conditions again by using the analytical condition administration module 306.

Next, the UI module 303 displays the analysis status while executing the analysis by using the virtual unit module 309 (S46). In step 46, the virtual unit module 309 controls the input column 326 and the output column 327 of the research work processing section 312 by using the GUI control script storage table stored in the GUI control script data base 310, executes the analysis, and receives the analysis status. Next, the UI module 303 receives the analysis result from the virtual unit module 309 and displays it (S47).

FIG. 8 is a drawing illustrating an example of a GUI control script storage table 801 stored in a GUI control script database 310. The GUI control script storage table 801 consists of a GUI control script ID storage area 801 to identify the operating procedure, and a GUI control script storage region 803.

Figure 9:
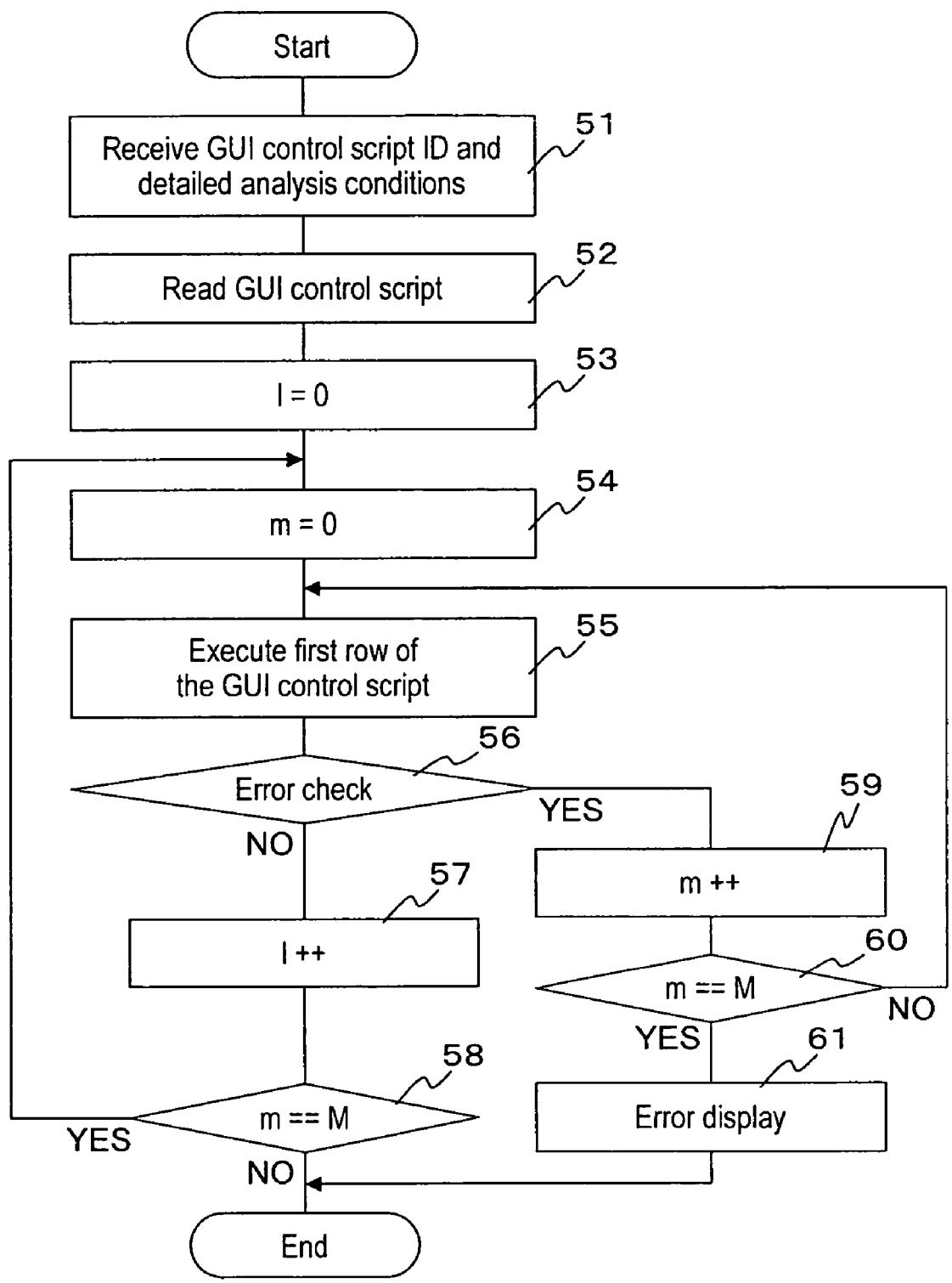
FIG. 9 is a processing flow when a virtual unit module controls an input column and an output column by using a GUI control script.

FIG. 9 is a processing flow in the case when the virtual unit module 309 controls the input column 326 and the output column 327 by using the GUI control script.

First of all, the virtual unit module 309 receives the GUI control script ID and the detailed analytical conditions from the UI module 303 (S51). Next, the virtual unit module 309 selects and reads the corresponding GUI control script from the GUI control script storage table 801 using the aforementioned GUI control script ID as a key (S52). Next, the virtual unit module 309 assigns 0 to the variable l which stores the number of rows of the executed GUI control script (S53). Then, the virtual unit module 309 assigns 0 to the variable m which stores the number of times retried to a specific row of the GUI control script (S54). Next, the virtual unit module 309 executes the lth row of the GUI control script by using the user interface message (S55). Next, the virtual unit module 309 decides whether an error occurs in step 55 (S56). When it is decided that an error does not occur in step 56, the virtual unit module 309 adds 1 to the variable l (S57). Next, the virtual unit module 309 decides if the variable l is equal to the constant L which indicates the number of rows of the GUI control script (S58). When it is decided that the variable l is equal to the constant L in step 58, this processing flow is terminated. When it is decided that the variable l is not equal to the constant L in step 58, step 54 is executed.

Moreover, when it is decided that an error occurs in step 56, the virtual unit module 309 adds 1 to the variable m (S59). Next, the virtual unit module 309 decides if the variable m is equal to the constant M which indicates the maximum value of the number of times retried (S60). When it is decided that the variable m is equal to the constant M in step 60, the virtual unit module 309 displays the error and terminates this processing flow (S61). When it is decided that the variable m is not equal to the constant M in step 60, step 55 is executed.

Figure 10:
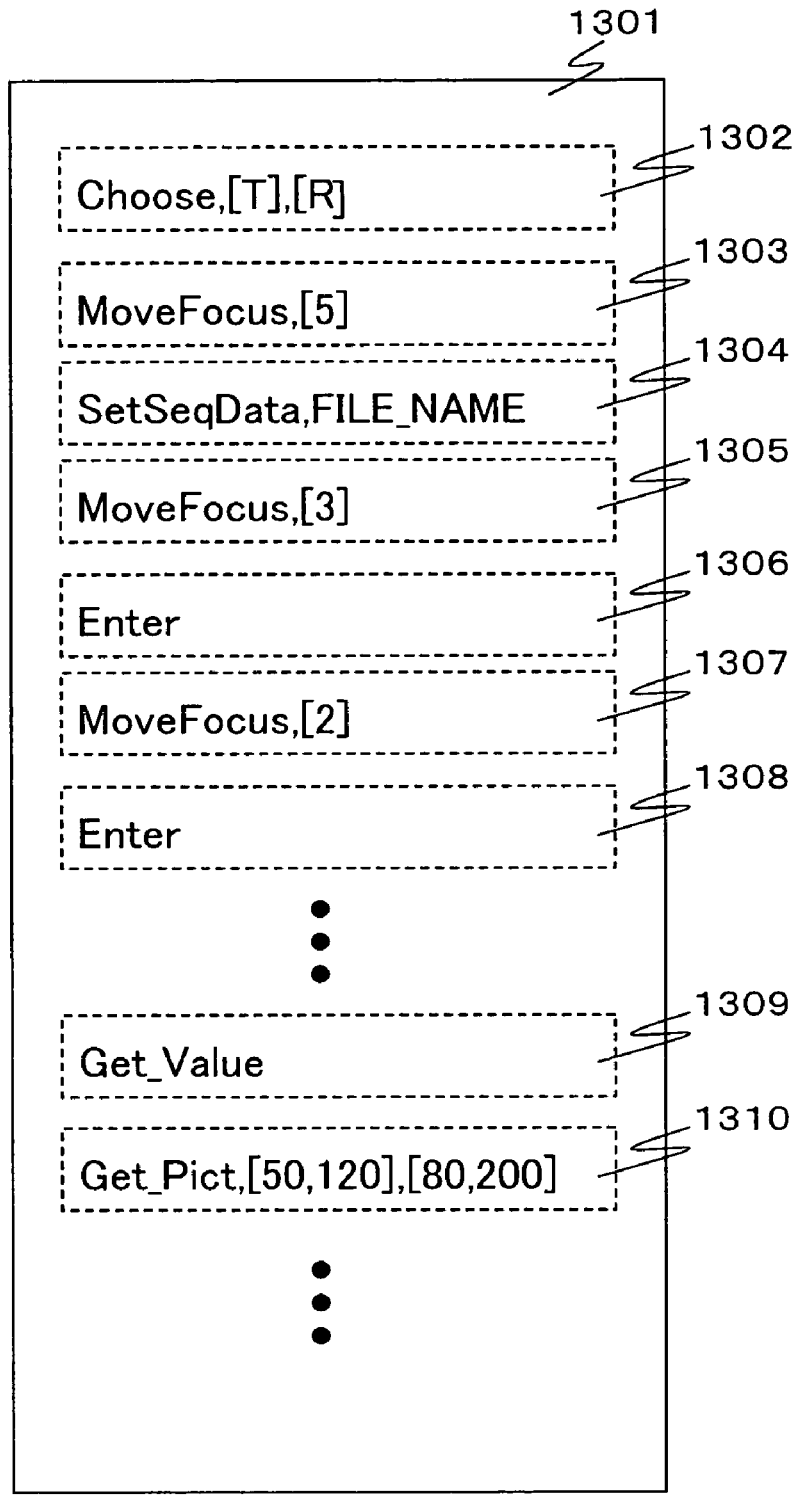
FIG. 10 is a drawing illustrating an example of a GUI control script.

FIG. 10 is a drawing illustrating an example of a GUI control script. Concretely, it is a drawing of a GUI control script for continuous analysis execution 1301 in which the GUI control script ID is 0x13. Hereinafter, how each row constituting the GUI control script for continuous analysis execution 1301 is executed will be shown.

In the execution of Choose, [T], [R] (1302), the virtual unit module 309 selects and opens a window which enables the sequence registration for continuous analysis from the window menu of the UI module 323 by sending the accelerator T and the accelerator R to the input column 326 of the UI module 323 using the user interface message. Moreover, in the execution of MoveFocus, [5] (1303), the virtual unit module 309 lets the mouse focus make five movements in the window of the UI module 323 by sending the user interface message and inputting tab depressions five times in the input column 326 of the UI module 323. Furthermore, in the execution of SetSeqData, FILE_NAME (1304), the virtual unit module 309 first replaces the FILE_NAME with a file name of the sequence file for continuous analysis specified in the detailed analytical conditions. Next, the virtual unit module 309 sets the file name of the sequence file for continuous analysis to the focused control in the window of the UI module 323 by sending the user interface message and inputting the file name of the sequence file for continuous analysis in the input column 326 of the UI module 323.

Moreover, in the execution of MoveFocus, [3] (1305), the virtual unit module 309 lets the mouse focus make three movements in the window of the UI module 323 by sending the user interface message and inputting tab depressions three times in the input column 326 of the UI module 323. Moreover, in the execution of Enter (1306), the virtual unit module 309 depresses the Enter button in the window of the UI module 323 by sending the user interface message and inputting Enter depression in the input column 326 of the UI module 323. In the execution of MoveFocus, [2] (1307), the virtual unit module 309 lets the mouse focus make two movements in the window of the UI module 323 by sending the user interface message and inputting tab depressions two times in the input column 326 of the UI module 323. Furthermore, in the execution of Enter (1308), the virtual unit module 309 depresses the Enter button in the window of the UI module 323 by sending the user interface message and inputting Enter depression in the input column 326 of the UI module 323.

In the execution of Get_Value (1309), the virtual unit module 309 reads a value from the focus control in the window of the UI module 323 by sending the user interface message and reading the value from the output column 327 of the UI module 323. Moreover, in the execution of Get_Pict, [50], [120] (1310), the virtual unit module 309 reads an image in a predetermined square region in the window of the UI module 323 by reading the image in the square region (50, 120) (80, 200) of the output column 327 of the UI module 323 using the user interface message.

As described in this embodiment, even if software having a track record in operation is updated or if it is totally different software, databasing a GUI control script makes it possible to apply without modification of routine work software by changing the GUI control script storage table stored in the GUI control script data base 310.

As described above, according to this embodiment, the amino acid analysis instrument 104 receives the fixed analytical conditions via the UI module 304 and receives variable analytical conditions via the UI module 303 to create detailed analytical conditions in the analytical condition administration module 306 based on the variable analytical conditions and the fixed analytical conditions. Next, the virtual unit module 309 controls the research work processing section (research work software) 312 based on the detailed analytical conditions. As a result, in an amino acid analysis instrument in which the processing conditions can be set in detail, it becomes possible that one achieves simplification of operations and the prevention of operation errors and software having a track record in operation installed in the amino acid analysis instrument is reused efficiently without modification.

In the aforementioned embodiment, although an example was demonstrated in which the present invention is applied to a processing instrument unit, the present invention also can be applied to distributed systems consisting of processing instruments and remote terminals. Hereinafter, an example in which the present invention is applied to distributed systems consisting of processing instruments and remote terminals will be described as a modified example of the aforementioned embodiment using FIG. 11.

Figure 11:
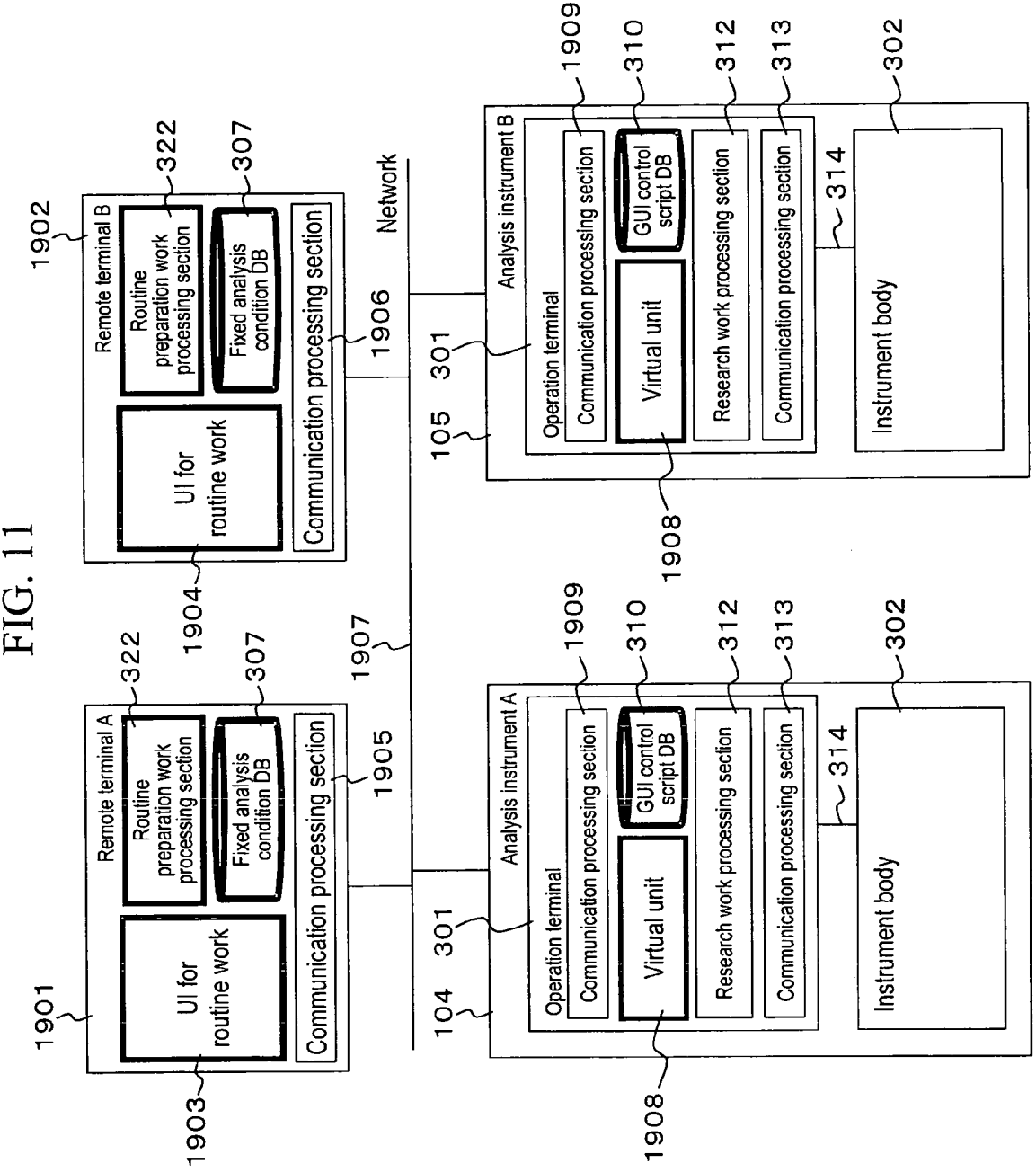
FIG. 11 is a drawing illustrating a configuration in which the present invention is applied to a distributed system.

FIG. 11 are drawings illustrating an example of a configuration in which the present invention is applied to a distributed system. This distributed system is constructed by connecting an analysis instrument A104, an analysis instrument B105, a remote terminal A1901, and a remote terminal B1902 with a network 1907. Moreover, the same as the aforementioned embodiment, the analysis instrument A104 is constructed by connecting the operation terminal 301 and the instrument body 302 to each other by using a communication cable 314. The operation terminal 301 consists of a virtual unit 1908, a communication processing section 1909 for communicating the virtual unit 1908 with the remote terminal A1901 and the remote terminal B1902, the GUI control script data base 310, the research work processing section 312, and the communication processing section 313. The analysis instrument B105 is assumed to be of the same configuration. The remote terminal A1901 consists of the UI1903 for routine work, the routine preparation work processing section 322, the fixed analytical condition data base 307, and the communication processing section 1905 for communicating the UI1903 for routine work with the virtual unit 1908. In this modified example, the remote terminal B1902 is assumed to be of the same configuration. Herein, the virtual unit 1908 is one which has a function of the virtual unit module 309 and it is achieved by the software. The UI1903 for routine work is one which has functions of the UI module 303 and the analysis condition administration module 306 and it is achieved by the software.

According to this modified example, even in the case when a routine analyst is at a place far from the amino acid analysis instrument 104, the routine work can be accomplished by using the remote terminal A1901 or the remote terminal B1902. Moreover, a researcher sometimes can confirm the analysis status by using the remote terminal B1902 while the routine analyst is performing the routine work by using the remote terminal A1901.

Furthermore, it is also possible that a routine analyst accomplishes routine analysis work using a plurality of analysis instruments such as the analysis instrument A104 and the analysis instrument B105 by using only the remote terminal A1901.

What is claimed is:

1. A processing instrument which displays the results of processing by receiving processing conditions comprising:
   an input section,
   a display section,
   a first processing section having a function which receives detailed processing conditions from said input section, a function which executes the processing according to the detailed processing conditions, and a function which displays the result of the processing in said display section, a fixed processing condition data base in which fixed processing conditions set to predetermined values are stored, a second processing section having a function which receives variable processing conditions which are a part of the detailed processing condition from said input section, a function which creates detailed processing conditions necessary for said first processing section by combining the variable processing conditions in question and the fixed processing conditions received from said fixed processing condition data base, a function which sends the created detailed processing conditions to said first processing section using a user interface message, and a function which receives a display content of the result of the processing from said first processing section and displays it in said display section; and wherein a GUI control script data base in which a GUI control script is stored is provided and the GUI control script which is stored in said GUI control script data base is referenced when said second processing section sends a user interface message to said first processing section.

2. A processing instrument according to claim 1, wherein said second processing section receives a display content of the result of the processing from said first processing section by sending a user interface message to said first processing section.

3. A processing instrument according to claim 2, wherein a GUI control script data base in which a GUI control script is stored is provided and the GUI control script which is stored in said GUI control script data base is referenced when said second processing section sends a user interface message to said first processing section.

4. A processing instrument according to claim 1, wherein an output screen from said second processing section is displayed in the foremost side of said display section and an input from said input section is received by said second processing section.

5. A processing instrument according to claim 1, wherein said second processing section has a function which displays a part of the screens or all of the screens among a screen to receive said variable processing conditions, a screen to validate said detailed processing conditions, and a screen to display the result of the processing.

6. A processing instrument according to claim 1, wherein said second processing section has a function which displays a screen in said display section to edit said fixed processing conditions.

7. A processing instrument system including a processing instrument to display the result of the processing by receiving processing conditions, a remote terminal, and a channel to connect said processing instrument to said remote terminal, wherein said processing instrument comprises a first processing section having a function which receives detailed processing conditions by input operations, a function which executes a processing according to the detailed processing conditions, and a function which outputs result of the processing in a display section, said remote terminal comprises an input section, a display section, a fixed processing condition data base which stores fixed processing conditions set to predetermined values, and a second processing section having a function which receives variable processing conditions which are a part of the detailed processing conditions from said input section, a function which creates detailed processing conditions necessary for said first processing section by combining the variable processing conditions in question and fixed processing conditions received from said fixed processing conditions, a function which sends the created detailed processing conditions to said first processing section using a user interface message, a function which receives a display content of the result of the processing from said processing section and displays it in said display section; and wherein a GUI control script data base in which a GUI control script is stored is provided and the GUI control script which is stored in said GUI control script data base is referenced when said second processing section sends a user interface message to said first processing section.

8. A processing instrument system according to claim 7, wherein
   a plurality of remote terminals are connected to said channel.

9. A processing instrument system according to claim 7, wherein
   a plurality of processing instruments are connected to said channel.

* * * * *

UNITED STATES PATENT AND TRADEMARK OFFICE
CERTIFICATE OF CORRECTION

PATENT NO.      : 7,594,175 B2                              Page 1 of 1
APPLICATION NO. : 11/348420
DATED           : September 22, 2009
INVENTOR(S)     : Tomita et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this

Fourteenth Day of December, 2010

David J. Kappos
*Director of the United States Patent and Trademark Office*